(12) United States Patent
Kangasniemi et al.

(10) Patent No.: US 7,001,181 B2
(45) Date of Patent: *Feb. 21, 2006

(54) APPLICATOR SYSTEM FOR DENTAL POSTS AND ANCHORS AND USE OF SAID APPLICATOR SYSTEM

(75) Inventors: Ilkka Kangasniemi, Piispanristi (FI); Pekka Vallittu, Kuusisto (FI)

(73) Assignee: Stick Tech Oy, Turku (FI)

( * ) Notice: Subject to any disclaimer, the term of this patent is extended or adjusted under 35 U.S.C. 154(b) by 154 days.

This patent is subject to a terminal disclaimer.

(21) Appl. No.: 10/483,292

(22) PCT Filed: Jul. 10, 2002

(86) PCT No.: PCT/FI02/00625

§ 371 (c)(1), (2), (4) Date: Apr. 9, 2004

(87) PCT Pub. No.: WO03/005927

PCT Pub. Date: Jan. 23, 2003

(65) Prior Publication Data

US 2004/0166472 A1 Aug. 26, 2004

Related U.S. Application Data

(63) Continuation of application No. 09/900,878, filed on Jul. 10, 2001, now Pat. No. 6,595,776.

(51) Int. Cl.
- A61C 5/02 (2006.01)
- A61C 5/04 (2006.01)
- A61C 5/08 (2006.01)

(52) U.S. Cl. ............ 433/81; 433/89; 433/220; 433/224

(58) Field of Classification Search .......... 433/81, 433/89–90, 220–221, 224
See application file for complete search history.

(56) References Cited

U.S. PATENT DOCUMENTS 3,968,567 A * 7/1976 Nevins .............. 433/224
4,472,141 A 9/1984 Dragan ............. 433/90
5,165,893 A 11/1992 Thompson ......... 433/224
5,295,828 A 3/1994 Grosrey ............ 433/81
5,445,523 A 8/1995 Fischer et al. .... 433/90
5,464,348 A 11/1995 Fischer et al. .... 433/26
5,816,816 A 10/1998 Scharf ............. 433/220
5,915,970 A 6/1999 Sicurelli, Jr. et al. .... 433/220
5,919,044 A 7/1999 Sicurelli, Jr. et al. .... 433/220
5,934,903 A 8/1999 Marlin ............. 433/81
5,964,592 A 10/1999 Hites et al. ....... 433/221
6,183,253 B1 2/2001 Billet et al. ....... 433/81
6,270,348 B1 * 8/2001 Petersen .......... 433/228.1
6,386,865 B1 5/2002 Suh et al. ......... 433/27

FOREIGN PATENT DOCUMENTS

WO    WO 98/52486    11/1998

OTHER PUBLICATIONS

Vallittu, "Ultra–High Modulus Polyethylene Ribbons as Reinforcement for Denture Polymethyl Methacrylate: A Short Communication", *Dental Materials* 13:381–382 (Nov. 1997).

* cited by examiner

Primary Examiner—John J Wilson
(74) Attorney, Agent, or Firm—James C. Lydon

(57) ABSTRACT

The invention relates to an applicator system (1) for application of a prefabricated reinforced composite post or anchor in its non-cured form into a dentinal canal (3). The invention is characterized in that the applicator system (1) comprises a prefabricated fiber-reinforced composite post or anchor in its non-cured form comprising a matrix and fibers, and an applicator tube (5) having a first end and a second end, wherein the inner diameter $d_T$ of said tube (5) is at most 5% larger than the outer diameter $D_{P/A}$ of said post or anchor in its non-cured form, and the outer diameter $D_T$ of the second end of said tube (5) through which the post or anchor is applied into the dentinal canal (3) is 0,5–2 mm. The invention further relates to the use of said applicator system.

12 Claims, 1 Drawing Sheet

APPLICATOR SYSTEM FOR DENTAL POSTS AND ANCHORS AND USE OF SAID APPLICATOR SYSTEM

This application is a U.S. National Stage of International application PCT/FI02/00625, filed Jul. 10, 2002, and is a continuation of U.S. application Ser. No. 09/900,878, filed Jul. 10, 2001, now U.S. Pat. No. 6,595,776.

FIELD OF INVENTION

This invention relates to an applicator system for application of a prefabricated reinforced composite post or anchor in its non-cured form into a dentinal canal. This invention further relates to the use of the system.

BACKGROUND OF THE INVENTION

The publications and other materials used herein to illuminate the background of the invention, and in particular, cases to provide additional details respecting the practice, are incorporated by reference.

Existing systems for anchorage of dental constructions such as crowns and large fillings to remaining roots are based on the use of dental posts mostly made of high rigidity materials like metal alloys, ceramics or to reduce the rigidity they can be made of completely polymerized fiber reinforced composite materials as disclosed e.g. in U.S. Pat. No. 5,964,592. Common characteristics of these posts are that when they are delivered and thus when they are inserted, they are in their final straight shape and that they are rigid. Occasionally they exhibit tapered or structured surfaces for increased mechanical retention for the composite luting cements. The earliest fiber reinforced composite (FRC) posts were made of carbon/graphite fibers with epoxy polymer matrix resulting in flexural modulus of 40 to 60 GPa. The most recent FRC posts are made of glass or silica fibers with an epoxy or dimethacrylate polymer matrix having flexural modulus between 28 to 40 GPa. Clinically the advantage of FRC posts has been that these do not cause fracturing of roots even if they have been used in short post lengths compared to the length of the clinical crown. On the other hand, the fracture incidence with metallic and ceramic posts has been high. The biggest disadvantages of completely polymerized FRC posts are the low bonding strength between the FRC post and the composite luting cement or composite core material, and the inability to bend along the curved root canal. All commercially available FRC posts require preparing the root canal to the standardized form of the FRC post. The preparation reduces the quantity of dentine and thus, reduces strength of the remaining root. These shortcomings cause frequent debonding of the FRC posts from the core and cement and hamper seriously the preparation of curved root canals. As a result of the present preparation techniques perforation of the tooth root and the periodontal ligament often occurs resulting in an elevated risk of infection of periodontal tissues. On the other hand, if there is need for long post lengths, which is the case when using metallic or ceramic posts to reduce the functional stress at the end point of the post, the root canal sealing has been shown to deteriorate considerably. This can cause an infection, e.g. a periapical periodontitis. Therefore a post system with an improved bonding characteristic that can be placed in curved individually shaped root canals even with short post lengths would be a welcome improvement.

It is known that polyethylene fiber products are being marketed for making posts in situ. The polyethylene fibers are inserted into the root with a special handheld instrument by pushing the fiber ribbon from the middle. The root canal is filled with a dual curing composite to wet the fibers and to bond the post to the tooth root surface. The potential advantages of this system are that there is no interface between the post polymer matrix surface and the cement since it is of the same material and that there is no need to prepare straight cavities for the posts. Disadvantages of a polyethylene fiber post system are that wetting of the fibers by the polymer matrix and bonding of the fibers to the polymer matrix are inadequate (Vallittu, Ultra-high-modulus polyethylene ribbon as reinforcement for denture polymethyl methacrylate. Dent Mater 1997;13:381–382), the control of wetting the fibers inside the root is impossible and use of woven fibers results in less than optimal orientation of the fibers in the root.

The state of the art fiber reinforcement material in dentistry is preimpregnated unidirectional glass fiber material as disclosed e.g. by Sicurelli & Masyr (WO 98/52486). There are four such materials available commercially: Jeneric Pentron's Fibrekor®, Ivoclar-Vivadent's Vectris®, Stick Tech's Stick® and everStick™. These differ from the other fiber materials in two respects: the bonding between the fiber surface and the polymer matrix is significantly higher than with polyethylene fibers and the wetting of the fibers with the polymer matrix is complete. This results in flexural strengths of up to 1280 MPa as compared to 350 MPa of the best polyethylene product and in elastic modulus of up to 28 GPa as opposed to 3–5 GPa of polyethylene composites.

The disadvantage of unidirectional glass fibers is their poor controllability in the clinical handling process. Considering a root canal of dimensions approximately 2 mm opening diameter and 1 mm end diameter, 5–10 mm length and being of considerable curvature imposes various problems for the insertion of a unidirectional, non woven, non twisted glass fiber bundle of approximately 1000 to 6000 individual fibers, impregnated with a low viscosity monomer liquid. The fibers fray, bend and tangle with each other when one tries to push them inside the canal. Once spread, it is next to impossible to collect the fibers back into order and try again.

Very similar devices to posts are root canal anchors called root canal screws that are actually just very short posts. These are manufactured in the form of a metallic screw of maximum length of approximately 10 mm and minimum length of 3 mm. In fact the division between an anchor and a post is not clear. In both cases however the root canal is prepared with a separate straight drill to make a close fit cavity for the screw. On the other hand, the screws can also be placed into other dentinal cavities and canals, such as those prepared in a vital tooth. These vital tooth screws are called parapulpal posts and they are most often used to improve retention of fillings to remaining teeth.

The indication for an anchor is the need for added fixation of a partial crown or filling of large dimensions. Fillings are generally attached through mechanical or chemical retention or both. The strength of chemical retention depends on bonding surface area and roughness and the chemical nature of the bond. Mechanical retention depends solely on the shape and surface roughness of the cavity. One could say that the less of the tooth is left for mechanical or chemical bonding the more important it is to create increased retention of posts and anchors. In this sense a crown with very little tooth support left is an extreme case of a filling and is a clear indication for a root canal post. The other extreme is a one-wall filling that in practice usually does not need any additional retention from a post nor an anchor. With larger cavities involving 2 or 3 walls, larger than that being already considered crowns, the achievable retention is dramatically reduced and there is an increasing need to create more retention artificially.

OBJECT AND SUMMARY OF THE INVENTION

The object of the present invention is to provide an alternative and/or improved system for application of a reinforced composite post or anchor into a dentinal canal. The object of the present invention is spesifically to provide a system for application of a post or anchor that does not have the above-mentioned drawbacks and that allows the positioning of a post or anchor without the fibers fraying, bending and tangling with each other.

The invention is defined in the appended claims.

The present invention concerns an applicator system for application of a prefabricated reinforced composite post or anchor in its non-cured form into a dentinal canal. The invention is characterized in that the applicator system comprises a prefabricated fiber-reinforced composite post or anchor in its non-cured form comprising a matrix and fibers and an applicator tube having a first end and a second end, wherein the inner diameter $d_T$ of said tube is at most 5% larger than the outer diameter $D_{P/A}$ of said post or anchor in its non-cured form, and the outer diameter $D_T$ of the second end of said tube through which the post or anchor is applied into the dentinal canal is 0,5–2 mm.

The present invention further concerns the use of the applicator system for preparing permanent or temporary root canal posts for fixation of artificial crowns and/or for the treatment of endodontic and/or periapical infections, for making a root canal filling and for making a post and/or anchorage system that forms a continuous structure from the apex of the tooth to the coronal part of the tooth.

DETAILED DESCRIPTION OF THE INVENTION

Figure 1:
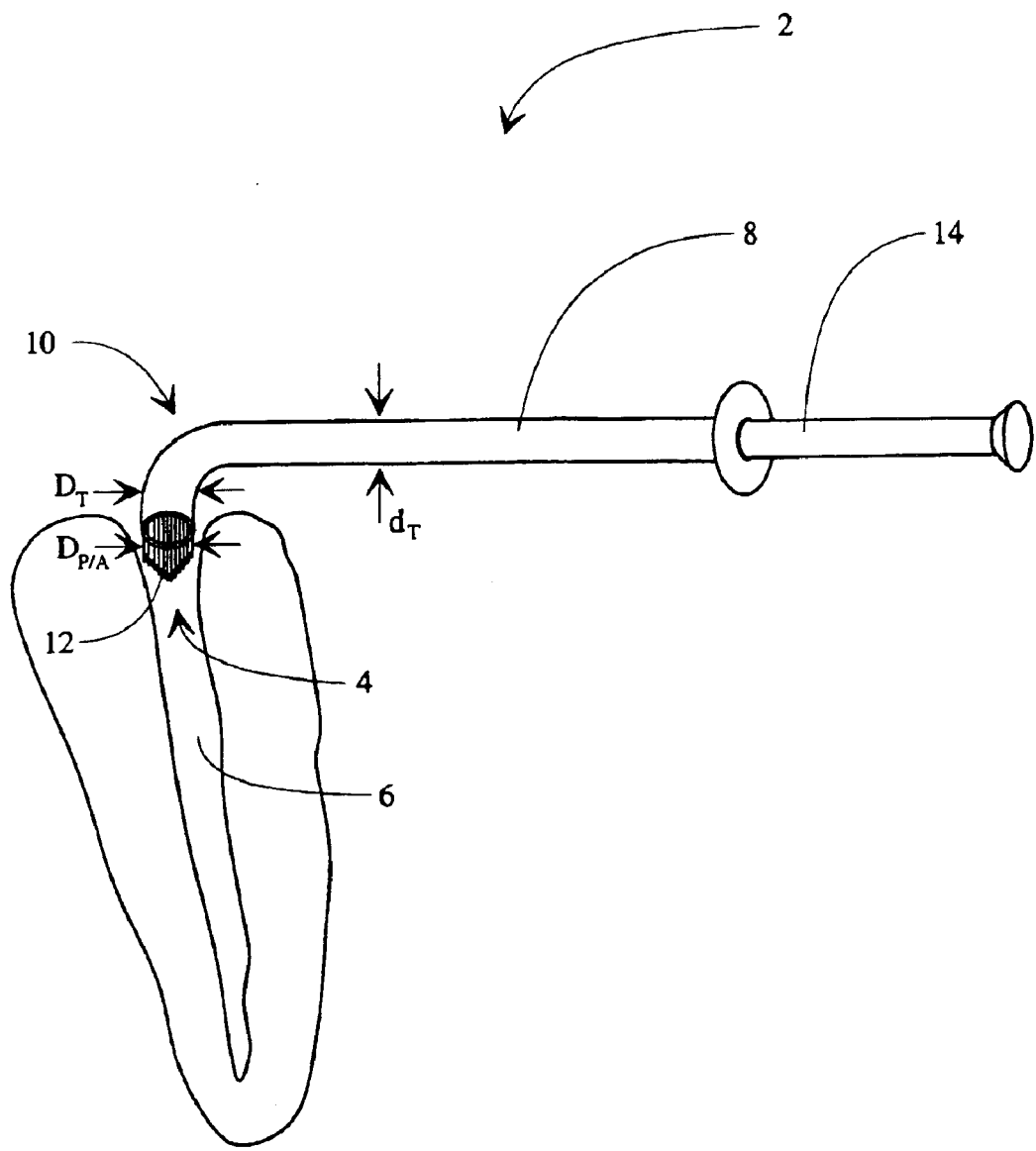
FIG. 1 shows the use of an applicator system according to the invention when applying a root canal post into the root canal.

The present invention provides an applicator system for application of a prefabricated reinforced composite post or anchor in its non-cured form into a dentinal canal. The invention is characterized in that the applicator system comprises a prefabricated fiber-reinforced composite post or anchor in its non-cured form comprising a matrix and fibers and an applicator tube having a first end and a second end, wherein the inner diameter $d_T$ of said tube is at most 5% larger than the outer diameter $D_{P/A}$ of said post or anchor in its non-cured form, and the outer diameter $D_T$ of the second end of said tube through which the post or anchor is applied into the dentinal canal is 0,5–2 mm. The inner diameter $d_T$ of said tube may be for example 4,5%, 4%, 3,75%, 2,4%, 2%, 1,5%, 0,9% or 0,2% larger than the outer diameter $D_{P/A}$ of said post or anchor.

In this context the dentinal canal refers to a root canal of a tooth or any canal of the tooth e.g. prepared for improving retention of fillings to remaining teeth by anchorage. By curing it is meant both polymerizing and cross-linking. The words "impregnating" and "wetting" may also be used interchangeably, i.e. a single fiber is wetted and a fiber bundle is either wetted or impregnated, both terms meaning that the material used for said wetting or impregnation is well distributed between the fibers and within the fiber bundle.

The present invention thus proposes an applicator system allowing the positioning of a post or anchor without diffi-culty. The use of an applicator according to the present invention ensures that the fibers of a finished post or anchor are in the same position with respect of each other than in the prefabricated post or anchor. The outer diameter of the second end of the tube through which the post or anchor is applied into the dentinal canal is chosen between 0,5–2 mm, so that its outer diameter is preferably essentially identical to the coronal opening of the root canal or other cavity in which the post of anchor is to be applied, or it is smaller than said opening or cavity.

The applicator system thus comprises a prefabricated fiber reinforced composite (FRC) post or anchor, also called a prepreg, i.e. a FRC post or anchor in its non-cured form, and a tube by which said prepreg can be pushed into a tooth canal. The prepreg comprises a matrix and fibers. The matrix may be composed of a monomer, a cross-linkable polymer or a mixture of a polymer and a monomer and optionally filler materials such as ceramic powder and/or opaquers, plasticizers etc. The matrix may also comprise one or several polymerization initiators. The material of the matrix may be any suitable material for dental applications, known to a person skilled in the art, such a poly(methyl methacrylate).

The fibers are preferably essentially continuous and/or essentially unidirectional. Fibers are most preferably used as a fiber bundle wherein the fibers are not twisted. The fibers are preferably glass fibers, silica fibers, carbon/graphite fibers, aramid fibers, Spectra®-fibers, Mylar®-fibers, polyethene fibers, polypropene fibers or other polyolefin fibers, quartz fibers, ceramic fibers such as aluminium oxide fibers, silica carbide fibers (SiC-fibers) or SiAlON-fibers.

The applicator tube may be stiff or flexible, transparent, opaque or partially opaque. The essential requirement is that the inner diameter $d_T$ of the tube is only slightly larger than the outer diameter $D_{P/A}$ of the FRC post or anchor, i.e. the diameter occupied by the volume of the fibers. Said inner diameter $d_T$ may be identical to said outer diameter or it may be at most 5% larger than said outer diameter. If in such confinement a force is applied to one end of the fibers the entire length of the fiber bundle moves inside the tube without being able to fray, bend or tangle. The end of the tube is placed directly on or marginally inside a root canal opening or the opening of a dentinal canal prepared to a vital tooth. The outer diameter $D_T$ of the tube is essentially the same or slightly smaller than the coronal opening of the canal, at most 5% smaller than said opening. Thus the canal forms a continuation of the tube thereby enabling trouble free transfer of the fibers into the canal. If nevertheless something goes wrong and the fibers are frayed, bent or tangled they can be pulled back into the tube which forces the fibers in perfect order again. The matrix of the post or anchor can be cured by light initiation and/or by autocuring in the dentinal canal. If the applicator tube is transparent and flexible it is easy to check the wetting of the fibers. If the fibers are prewetted the tube may also be opaque. In the latter case wetting can only be done using a light curing resin. The fibers of the post or anchor can comprise optical fibers allowing light curing of the matrix in the dentinal canal. It is thus possible to use the present applicator either such that the prefabricated post comprising both matrix and fibers is delivered within the applicator tube or that only the fibers are present in the applicator tube and the matrix is added shortly prior to the positioning of the post or anchor. Once the fibers are in place in the canal the outside portion of the fibers, i.e. the coronal part may be placed in any direction wished. This allows the dentist to direct the core part of the post or anchor in an optimal direction for building of the crown or filling. If the fibers are unidirectional this may be done without compromising the strength of the construction. Since the matrix of the post or anchor prepreg is cured in the root canal, with or without additional composite luting cement, the additional cements or dentine adhesives are chemically adhered to the FRC post or anchor during curing. After being cured in the root canal and twisted to the desired direction according to the angulation of the crown or filling to be made, the core particulate filler composite material is cured to the oxygen inhibition layer of the coronal part of the post or anchor. This results in a durable bond between the core composite and post or anchor. The fibers may be wetted at the factory with a light curing resin (prepreg) or at the dentist office using a dual curing resin. This is to say that in the embodiments according to the invention described above the fibers may or may not be prewetted with a matrix when sold.

For molar regions it may be preferential that the tube is temporarily or permanently shaped into an arch so as to be able to bring the tube to the canal opening from an optimal direction.

The end of the fiber bundle may be cut into a conical shape so that the tip of the bundle is pointed or blunt but only a fraction of the main fiber bundle is cut in such a way. Indeed, it is possible that an important part of the length of the post is truncated but not all of its length. This is to allow the shape of the fiber bundle to better fit to the shape of the root canal.

The insertion force may be applied to the end of the fibers by a separate piston well fitted to the diameter of the applicator tube. Another way is to precure the rear end of the fiber bundle, through which the insertion force is applied, into the shape of a piston. Typically about 1 to 2 mm of the rear end of a post of 5–10 mm is cured. Thus the fibers partially outside and partially inside the tube would be stiff whilst the other end of the fibers would be non-cured, elastic and maybe even non-impregnated with resin. However they may be preimpregnated with a polymer or a polymer-monomer gel according to earlier inventions disclosed by Vallittu et al. (WO 96/25911 and WO 99/45890) or with a monomer or any mixture containing monomer or polymer. Such mixtures could contain e.g. microfillers, opaquers or alike.

The tip of the prefabricated post could be cured into a shape that easily penetrates into the root canal and finally stops at the apex. The polymerized apical tip can additionally contain antimicrobial agents to heal the apical periodontal infections. The post or anchor can be used as a temporary or permanent root canal filling material.

The invention further relates to the use of an applicator system according to the invention for the production of a tooth canal filling. The invention also relates to the use of an applicator system according to the invention for preparing permanent or temporary root canal posts for fixation of artificial crowns, for the treatment of endodontic and/or periapical infections as well as for making a post and/or anchorage system that forms a continuous structure from the apex of the tooth to the coronal part of the tooth.

DETAILED DESCRIPTION OF THE DRAWING

FIG. 1 shows the use of an applicator system 1 according to the invention when applying a root canal post 2 into the root canal 3 of a tooth 4. The applicator system 1 comprises an applicator tube 5 having a first end 6 and a second end 7 through which the post 2 is applied into the dentinal canal 3. The FIGURE illustrates the dimensions mentioned, the inner diameter $d_T$ of the applicator tube 5, the outer diameter $D_{P/A}$ of the post 2 and the outer diameter $D_T$ of the second end 7 of the tube 5.

The FIGURE further shows a separate piston 8 of the applicator system by which the post 2 is pushed through the second end 7 of the applicator tube 5. The end of the fiber bundle forming the post together with the matrix is cut into a conical shape so that it fits better to the shape of the bottom of the root canal 3. The applicator tube 5 is shaped into an arch so as to be able to bring the tube 5 to the canal opening from an optimal direction.

In this specification, except where the context requires otherwise, the words "comprise", "comprises" and "comprising" means "include", "includes" and "including", respectively. That is, when the invention is described or defined as comprising specified features, various embodiments of the same invention may also include additional features. Also, the reference signs should not be construed as limiting the claims.

What is claimed is:

1. An applicator system for application of a prefabricated reinforced composite post or anchor in its non-cured form into a dentinal canal, comprising
    a) a prefabricated fiber-reinforced composite post or anchor in its non-cured form having an outer diameter $D_{P/A}$ and comprising a matrix and fibers, and
    b) an applicator tube having a first end and a second end, wherein
        i) an inner diameter $d_T$ of said tube is at most 5% larger than the outer diameter $D_{P/A}$ of said post or anchor in its non-cured form, and
        ii) an outer diameter $D_T$ of the second end of said tube through which the post or anchor is applied into the dentinal canal is 0.5–2 mm, and
    wherein said prefabricated composite post or anchor is positioned inside said applicator tube.

2. The applicator system of claim 1, wherein said fibers of said post or anchor are essentially continuous and essentially unidirectional.

3. The applicator system of claim 1, wherein said fibers are glass, silica, carbon, graphite, aramid, polyethene, polypropene, quartz, aluminium oxide, silica carbide or SiAlON fibers.

4. The applicator system of claim 1, wherein said applicator tube is flexible or rigid.

5. The applicator system of claim 1, wherein said applicator tube is transparent or opaque.

6. The applicator system of claim 1, wherein said matrix of the post or anchor is light curable or autocurable.

7. The applicator system of claim 1, wherein the post or anchor comprises optical fibers.

8. The applicator system of claim 1, wherein the end of the post or anchor first applied into the root canal is precured and/or wetted with antimicrobial agents.

9. The applicator system of claim 1, wherein only the fibers of said prefabricated composite post or anchor are positioned inside said applicator tube.

10. A method for making a tooth canal filling, comprising,
    i) applying a reinforced, non-polymerized composite post or anchor into a dentinal canal by means of the applicator system of claim 1, and
    ii) polymerizing said post or anchor.

11. The method of claim 10, wherein said post or anchor is suitable for fixation of artificial crowns and/or for the treatment of endodontic, and/or periapical infections.

12. The method of claim 10, wherein said post or anchor is part of a continuous structure from the apex of the tooth to the coronal part of the tooth.

* * * * *